(12) United States Patent
Li et al.

(10) Patent No.: US 11,448,576 B2
(45) Date of Patent: Sep. 20, 2022

(54) MULTIFUNCTIONAL TRUE TRIAXIAL ROCK DRILLING TEST SYSTEM AND METHOD

(71) Applicants: SHANDONG UNIVERSITY, Shandong (CN); SHANDONG TIANQIN ENGINEERING TECHNOLOGY CO., LTD., Shandong (CN)

(72) Inventors: Shucai Li, Jinan (CN); Qi Wang, Jinan (CN); Bei Jiang, Jinan (CN); Hongke Gao, Jinan (CN)

(73) Assignees: SHANDONG UNIVERSITY, Jinan (CN); SHANDONG TIANQIN ENGINEERING TECHNOLOGY CO., LTD., Heze (CN)

( * ) Notice: Subject to any disclaimer, the term of this patent is extended or adjusted under 35 U.S.C. 154(b) by 928 days.

(21) Appl. No.: 16/314,603

(22) PCT Filed: Jan. 7, 2017

(86) PCT No.: PCT/CN2017/070553
§ 371 (c)(1),
(2) Date: Apr. 4, 2019

(87) PCT Pub. No.: WO2018/006585
PCT Pub. Date: Jan. 11, 2018

(65) Prior Publication Data
US 2020/0386659 A1 Dec. 10, 2020

(30) Foreign Application Priority Data

Jul. 6, 2016 (CN) .......................... 201610529362.9
Jul. 6, 2016 (CN) .......................... 201610529764.9

(51) Int. Cl.
*G01N 3/10* (2006.01)
*E21B 44/04* (2006.01)
(Continued)

(52) U.S. Cl.
CPC ............... *G01N 3/10* (2013.01); *E21B 44/04* (2013.01); *E21B 49/003* (2013.01); *E21B 49/02* (2013.01);
(Continued)

(58) Field of Classification Search
CPC ............ G01N 3/10; G01N 3/18; G01N 33/24; G01N 2203/0019; G01N 2203/0048; E21B 44/04; E21B 49/003; E21B 49/02
See application file for complete search history.

(56) References Cited

U.S. PATENT DOCUMENTS 6,729,190 B1    5/2004 Boyko et al.
6,801,814 B1 *  10/2004 Wilson ..................... E02D 3/12
                                                    702/158
(Continued)

FOREIGN PATENT DOCUMENTS

CN    101504356 A    8/2009
CN    102011582 A    4/2011
(Continued)

OTHER PUBLICATIONS

Liu et al., Field Tests and Analytical Model for Estimating the Effects of Anchor-root at the Bottom of Full-length Bond Bolt, 2009 International Conference on Information Engineering and Computer Science, Dec. 2009 (Year: 2009).*
(Continued)

*Primary Examiner* — Toan M Le
*Assistant Examiner* — Xiuqin Sun
(74) *Attorney, Agent, or Firm* — Oliff PLC

(57) ABSTRACT

A multifunctional true triaxial rock drilling test system and method; rock cores are respectively taken from a plurality of
(Continued)

drilling holes on the same test piece, uniaxial test and triaxial test are respectively performed on these rock cores to obtain multiple groups of mechanical property parameters, multiple groups of drilling parameters are obtained according to a multifunctional true triaxial rock drilling tester that can directly measure the drilling parameters, relational expression between mechanical property parameters of rock mass and the drilling parameters is established, and mechanical property parameters of rock mass can be obtained just by detecting the drilling parameters of the rock mass through the relational expression. The multifunctional true triaxial rock drilling tester is preset test device, has function of performing triaxial loading on the test piece, and can simulate drilling process of drilling rig in a three-way confining pressure state in underground engineering of the test piece.

21 Claims, 4 Drawing Sheets

(51) Int. Cl.
| | | |
|---|---|---|
| | *E21B 49/00* | (2006.01) |
| | *E21B 49/02* | (2006.01) |
| | *G01N 3/18* | (2006.01) |
| | *G01N 33/24* | (2006.01) |

(52) U.S. Cl.
CPC .............. *G01N 3/18* (2013.01); *G01N 33/24* (2013.01); *G01N 2203/0019* (2013.01); *G01N 2203/0048* (2013.01)

(56) References Cited

U.S. PATENT DOCUMENTS

| | | | |
|---|---|---|---|
| 9,091,779 B2 | 7/2015 | Li et al. | |
| 2017/0218733 A1* | 8/2017 | Jain | .................. E21B 43/00 |

FOREIGN PATENT DOCUMENTS

| | | | | | |
|---|---|---|---|---|---|
| CN | 102288742 | A | | 12/2011 | |
| CN | 102607941 | A | | 7/2012 | |
| CN | 102621012 | A | | 8/2012 | |
| CN | 103091222 | A | | 5/2013 | |
| CN | 103868799 | A | | 6/2014 | |
| CN | 103994899 | A | | 8/2014 | |
| CN | 104034592 | A | | 9/2014 | |
| CN | 104198311 | A | * | 12/2014 | |
| CN | 104655495 | A | | 5/2015 | |
| CN | 104792616 | A | | 7/2015 | |
| CN | 104807960 | A | | 7/2015 | |
| CN | 204613077 | U | | 9/2015 | |
| CN | 105223093 | A | | 1/2016 | |
| CN | 105547849 | A | * | 5/2016 | ........... G01N 15/082 |
| CN | 105758730 | A | | 7/2016 | |
| CN | 105938070 | A | | 9/2016 | |
| CN | 106018100 | A | | 10/2016 | |
| FR | 2347526 | A1 | | 11/1977 | |
| GB | 1572556 | A | | 7/1980 | |
| WO | 0240965 | A2 | | 5/2002 | |

OTHER PUBLICATIONS

Mar. 29, 2017 Written Opinion issued in International Patent Application No. PCT/CN2017/070553.
Office Action in Chinese Patent Application No. 201610529362.9, dated Jul. 6, 2016.
Search Report issued in Chinese Patent Application No. 2016105297649, dated Jul. 6, 2016.
Search Report issued in Chinese Patent Application No. 2016105293629, dated Jul. 6, 2016.
Yasar et al. "An experimental investigation into the drilling and physico-mechanical properties of a rock-like biillle material." Journal of Petroleum Science and Engineering, Jan. 23, 2011, vol. 76, pp. 185-193.
Jin et al. "Experimental Investigation on Mechanical Property of Reinforced Fractured Rock." Chinese Journal of Rock Mechanics and Engineering, May 2012, vol. 31, pp. 3395-3398.
Chen et al. "Study on identification along with drilling of roof strata of excavation roadway." Journal of Mining & Safety Engineering, Mar. 2016, vol. 33, No. 2, pp. 271-277.
Mar. 29, 2017 International Search Report issued in International Patent Application No. PCT/CN2017/070553.

* cited by examiner

MULTIFUNCTIONAL TRUE TRIAXIAL ROCK DRILLING TEST SYSTEM AND METHOD

FIELD OF THE INVENTION

The present invention relates to the technical field of geotechnical engineering investigation, in particular to a multifunctional true triaxial rock drilling test system and method.

BACKGROUND OF THE INVENTION

It is relatively frontier at present that a relevance research is made by using drilling parameters (torque, rotating speed, drilling pressure, drilling rate, drilling specific work), rock mechanics parameters (uniaxial compressive strength, Poisson's ratio, internal friction angle, modulus of elasticity), and rock mass characteristics (fracture width, quantity and rock mass integrity coefficient) in a drilling process of a drilling rig. The method has the advantages of being visual, efficient and able to perform onsite real-time judgment because no rock core is collected in the drilling process, and the rock mass mechanical parameters are directly characterized by using the drilling parameters of the drilling rig. At present, few indoor test devices for the research are available and have the following defects:

(1) A device for applying a confining pressure and an axial pressure is not employed, and the rock at an underground engineering site is generally in a three-way pressure state, which results in a larger difference between drilling conditions of the existing test device and conditions at the engineering site.

(2) Thermodynamic coupling conditions cannot be applied to a rock mass test piece, the influence of thermal coupling of the rock mass on the drilling parameters of the drilling rig cannot be researched, and the mechanical properties of the rock mass under the action of the thermal coupling cannot be researched.

The traditional common methods for evaluating the reinforcement effect after surrounding rock anchoring and grouting include a transient electromagnetic method, a geological radar method and a drilling method, but these methods have the following problems:

(1) due to the complexity of the geological conditions at the construction site, it is often difficult to obtain accurate results by using the transient electromagnetic method and the geological radar method, and the transient electromagnetic method and the geological radar method can only be used for performing qualitative analysis and judgment on the reinforced weak surrounding rock via images, but cannot be used for realizing accurate quantitative analysis of the reinforcement effect.

(2) In the application of the drilling method, the time interval from onsite core collection to experimental report acquisition is long, which seriously restricts the construction progress and increases the engineering budget cost.

(3) During drilling in weak and fractured stratum, a rock core collection rate and the integrity are difficult to be ensured, so that the physical properties and mechanical parameters of the local rock formation cannot be obtained, and as a result, the changes of the mechanical parameters of the rock before and after grouting cannot be quantitatively compared.

At present, neither an experimental device for drilling parameter test and drilling process research under three-way confining pressure conditions, nor a method for evaluating an anchoring and grouting effect of a monitoring device based on drilling parameter is disclosed.

SUMMARY OF THE INVENTION

The objective of the present invention is to provide a multifunctional true triaxial rock drilling test system, which can complete drilling of a drilling rig under multi-directional confining pressure conditions, and an operation parameter measurement test of the drilling rig in a drilling process.

A second objective of the present invention is to provide a control method of the multifunctional true triaxial rock drilling test system. The system can be effectively controlled according to the method to obtain accurate measurement data.

A test method for characterizing rock mass characteristics by using drilling parameters in underground engineering is also provided. In the test method, the rock mass characteristics are characterized by using drilling parameters (drilling rate, torque, rotating speed, drilling pressure, drilling specific work), the relationship between the drilling parameters and the mechanical parameters (uniaxial compressive strength, cohesive force, internal friction angle, modulus of elasticity) of rock mass, and rock mass integrity parameters RQD can be established, it is convenient to detect the performance of the rock mass, and the time for performing a triaxial test and a uniaxial test on the rock core can be saved.

A fourth objective of the present invention is to provide a method for evaluating an anchoring and grouting reinforcement effect based on drilling parameters. The method provides a test use of the true triaxial rock drilling test system of the present invention, represents one of the functions of the test system, gives the evaluation method of the anchoring and grouting reinforcement effect and has important application significance.

In order to achieve the above objectives, the present invention adopts the following technical solutions:

The first solution provided by the present invention is as follows: a multifunctional true triaxial rock drilling test system includes a pressure loading device, a drilling rig unit, a monitoring control unit and a hydraulic station, wherein the hydraulic station provides power for the pressure loading device, and the pressure loading device applies a confining pressure to a rock test piece placed therein;

the drilling rig unit is arranged at an upper end of the pressure loading device for drilling the rock test piece under the application of the three-way confining pressure;

the monitoring control unit controls the pressure loading device to apply the pressure, and also controls either of two groups values of the drilling rig, namely a torque and a rotating speed, and a drilling pressure and displacement.

The test piece may have any size ranging from 100 mm×100 mm×150 mm to 300 mm×300 mm×600 mm, and by changing loading plates of different sizes and placing steel cushion blocks of different sizes at the upper side and the lower side of the test piece, a loading rod acts on the center of the side face of the test piece to apply confining pressures to the cushion blocks of different sizes.

The pressure loading device includes a pressure chamber, and a confining pressure loading device is arranged on the outer side of the pressure chamber to apply the confining pressure to the rock test piece.

A platform plate is fixedly connected below a reaction force frame, the platform plate is directly in contact with the rock test piece, and reserved holes are formed in the middle of the platform plates and the reaction force frame to allow passage of a drill pipe of the drilling rig.

A test piece platform for carrying the pressure chamber and the rock test piece is arranged at the lower end of the pressure chamber.

Further, the confining pressure loading device includes two groups of vertically arranged lateral loading plates, each group of lateral loading plates includes two opposite lateral loading plates arranged in parallel, and the two groups of lateral loading plates form a rectangular loading structure to surround the test piece in the pressure chamber.

The application pressures of the two groups of lateral loading plates are different or the same, so that the confining pressure application of the test piece under various confining pressure conditions can be realized.

The confining pressure loading device further includes a lateral hydraulic oil cylinder, the hydraulic oil cylinder drives a piston rod to push the lateral loading plate to apply a horizontal pressure to the test piece, and the end part of the lateral hydraulic oil cylinder is embedded in a lateral reaction force plate for providing a supporting reaction force for the lateral hydraulic oil cylinder.

The drilling rig unit includes a drilling rig embedded in a drilling rig slide rail, the drilling rig axially moves up and down along the drilling rig slide rail, the drilling rig slide rail is fixed on the reaction force frame at the top of the test piece through a drilling rig slide rail fixing plate, the drilling rig is fixedly connected with a drilling rig servo motor and moves downward or upward under the push or pull of a drilling rig top hydraulic oil cylinder at the upper part.

The drilling rig servo motor provides a rotating force for the drilling rig, and the drilling rig top hydraulic oil cylinder provides a downward pressure for the drilling rig, and the drill pipe of a drilling bit of the drilling rig is in contact with the test piece via the reserved holes in the reaction force frame and the loading plate at the top of the test piece to generate a drilling function.

The drilling rig unit further includes a servo motor, a speed reduction mechanism and a belt transmission device, the belt transmission device and the speed reduction mechanism constitute a two-stage speed reduction mechanism, the speed reduction multiples are changed with the diameter ratio of gears at both ends of a belt in the belt transmission device, the upper part of the drilling rig is fixedly connected to the drilling rig top hydraulic oil cylinder which provides an axial force for the drilling rig, and the drilling rig servo motor provides a rotating force for the drilling rig.

The monitoring control unit includes a monitoring unit, and specifically includes a lateral confining pressure sensor for detecting lateral confining pressures of upper sides on four directions, a lateral displacement sensor for detecting a moving distance of the lateral loading plate, and a drilling rig torque sensor for detecting the torque of the drilling rig, a drilling rig rotating speed sensor for detecting the rotating speed of the drilling rig, a drilling rig pressure sensor for detecting a pressure applied by the drilling rig downward, and a drilling rig displacement sensor for detecting the vertical moving distance of the drilling rig; and the monitoring control unit further includes an axial pressure sensor arranged at an axial hydraulic oil cylinder, the lateral confining pressure sensor is arranged on an oil supply pipeline, the lateral displacement sensor is arranged on the side of the lateral hydraulic oil cylinder, and the servo motor has a rotating speed sensor.

In a preferred solution, four pressure sensors, four displacement sensors and one torque sensor are contained in total, the servo motor has the rotating speed sensor, the torque sensor is connected with the drill pipe at one end and is connected with a main shaft of the drilling rig at the other end, and the pressure and displacement sensors respectively monitor the pressure and the displacement of the drilling rig top hydraulic oil cylinder at the upper part of the drilling rig, an axial loading device and a two-direction confining pressure loading device, the pressure sensors are installed on the oil supply pipelines of the four oil cylinders, and the displacement sensors are fixed on the side faces of the oil cylinders to measure the position changes of the oil cylinders and the corresponding loading plates.

The monitoring control unit includes a control unit, specifically including a logic controller, a power amplifier and a servo motor, the logic controller receives signals of the pressure sensor, the displacement sensor and the torque sensor, compares the signals with a set value, sends a voltage instruction to control the drilling rig servo motor and a hydraulic station servo motor to work, and achieves closed-loop control, and the hydraulic station servo motor is connected with the axial hydraulic oil cylinder and the lateral hydraulic oil cylinder respectively.

A control method of the above multifunctional true triaxial rock drilling test system is provided, wherein the control unit controls the drilling rig in four modes:

A. controlling a torque and a drilling rate, and collecting a drilling pressure and a rotating speed;

B. controlling the torque and the drilling pressure, and collecting a rotating speed and a drilling rate;

C. controlling the rotating speed and the drilling rate, and collecting the torque and the drilling pressure;

D. controlling the rotating speed and the drilling pressure, and collecting the torque and the drilling rate.

By controlling two parameters and measuring the other two parameters, the parameter change can be manually controlled, an intuitive research is made on the influence of the changes of the controlled variables on the other drilling parameters and the response sensitivity to the rock mechanical parameters, and the following situations are avoided: the parameters in the drilling process of an ordinary drilling rig are unstable and the operation mode is single, such that it is difficult to study the relationship between the drilling parameters and the rock mechanical parameters. The control unit controls the hydraulic station servo motor to control the axial pressure and the confining pressure of the test piece in three control modes:

A. a constant strain loading mode, in which small strains occurring in the test piece within a unit time are the same;

B. a constant pressure incremental loading mode, in which the pressure increase of the hydraulic oil cylinder within the unit time is the same;

C. a constant force maintenance mode, in which the test piece is kept at a set confining pressure value.

The control method of constant strain loading of the test piece: the top of a uniaxial test piece contacts a platform plate below the reaction force frame, the uniaxial test piece is in the uniaxial compression state, the axial loading device is controlled to be in a constant strain loading mode, and the axial pressure is applied to the test piece at a loading speed suggested by the International Society for Rock Mechanics until the test piece is broken.

The control method of constant pressure incremental loading of the test piece: three main stresses of the rock mass test piece are independently applied, the constant pressure incremental loading is that the same pressure is applied to a certain side face of the test piece within the unit time. The working method is that the logic controller records the current pressure read by the lateral pressure sensor or the axial pressure sensor, and controls the servo motor to drive the oil cylinder to pressurize the test piece, the logic controller records the pressure change of the pressure sensor, and when the pressure reaches the preset increment within the unit time, the logic controller controls the servo motor to stop and repeats the above work within the next unit time.

In addition, the test system further includes an axial pressure loading device for applying the axial pressure to the rock test piece, the axial pressure loading device includes an axial hydraulic oil cylinder, an axial loading plate is arranged at the lower part of the test piece, and the axial hydraulic oil cylinder pushes the axial loading plate to drive the rock test piece to perform axial movement and contacts the reaction force frame to apply an axial force to the rock test piece.

The test piece platform is a platform for placing the test piece in the pressure chamber, and a positioning ball is arranged at the center of the platform for centering the test piece.

A steel heating plate is arranged at the outside of the pressure chamber, a curved heating pipeline is arranged in the heating plate, a pipeline inlet is welded on the upper end of one side face of the heating plate, a pipeline outlet is welded on the lower end of an opposite side face, so that water vapor or high temperature liquid passes through the pipeline to heat the test piece, and then the mechanical properties of the test piece under thermal coupling are studied.

In the case that the test piece contains water therein or is filled with fracture water, a sealing rubber box may be arranged at the bottom of the test piece platform, and a rubber cover slightly larger than the sealing rubber box may be arranged at the top of the test piece, a pore is reserved in the middle of the rubber cover, the axial and lateral loading plates apply the pressure to the rubber box and the rubber cover, and a three-way pressure is applied to the test piece through the rubber box and the rubber cover. This design can prevent the internal water from flowing outside, so that the test system can test the water-containing rock mass.

The drilling rig is a rotary cutting drilling rig or an impact drilling rig. The drilling bit of the rotary cutting drilling rig can be set as a core collection drilling bit or a non-core collection drilling bit.

The present invention has the function of a uniaxial testing machine. The uniaxial test piece is placed in the pressure chamber, the steel cushion blocks are placed at the upper side and the lower side of the uniaxial test piece, the axial loading device lifts the pressure chamber, so that the steel cushion blocks on the uniaxial test piece are in contact with the platform plate below the reaction force frame, so that the uniaxial test piece is in the uniaxial compression state, the axial loading device is controlled to be in a constant strain loading mode, and the axial pressure is applied to the test piece at the loading speed suggested by the International Society for Rock Mechanics until the test piece is broken.

The multifunctional true triaxial rock drilling test system can perform constant pressure incremental loading by using the axial pressure loading device and the confining pressure loading device, realize the independent application of the three main stresses of the rock test piece, and has a part of functions of a rock true triaxial testing machine.

The second solution provided by the present invention is as follows: a test method for characterizing rock mass characteristics by using drilling parameters in underground engineering. A drilling test is made by the multifunctional true triaxial rock drilling test system to obtain the drilling parameters of the test piece, and then multiple groups of rock cores are collected from the periphery of a drilling hole in the drilling test of the test piece. The rock core processing methods are different depending on different test objectives.

(1) A rock mass integrity parameter RQD value of the rock core is measured, and a relational expression between the rock mass RQD value and the drilling parameters is established;

(2) a uniaxial test and a triaxial test are carried out on these cores respectively to obtain mechanical property parameters of the test piece, and the relational expression between the mechanical property parameters of the rock mass and the drilling parameters is established.

Through the above relational expression, the integrity parameter RQD value and the mechanical property parameters of the rock mass can be obtained by simply detecting the drilling parameters of the rock mass. Of course, the curve of the relational expression is better to be stored in the monitoring control system of the true triaxial rock drilling tester, and the integrity parameters and mechanical properties of the rock mass can be obtained in real time according to the relational expression, which is simple and convenient.

Further, in order to measure the mechanical property parameters of the rock core test piece, the rock core is divided into a plurality of sections from top to bottom with a height of 100 mm, that is, the rock core is cut, polished and made into a rock standard test piece, and the mechanical property parameters of the sections are obtained respectively.

Further, when the relational expression between the rock mass integrity parameter RQD value and the drilling parameters is established, the test piece used is a fractured rock mass test piece.

Further, in order to achieve the objective of the present invention, the following specific steps are used:

Step 1) according to the test purpose, determining rock mass basic factors affecting the three-way confining pressure loading drilling, and designing a reasonable test plan;

step 2) preparing the corresponding test piece according to the test solution;

step 3) performing a three-way confining pressure drilling test on the prepared test piece, collecting the drilling parameters in a drilling process of the test piece during the test, and collecting the rock core of the test piece;

according to different test purposes, step 4) is performed in two ways:

step 4a) performing statistics on the core collection rate of the rock core of the test piece, and measuring the integrity parameter RQD value of the test piece;

step 4b) cutting and grinding the rock core obtained from the test piece to prepare a plurality of standard test pieces, and performing a triaxial test and a uniaxial test to measure the mechanical property parameters of the test piece material;

step 5) preprocessing the collected data, and then establishing the relationship between the processed data and the same-depth rock mechanical properties and rock mass integrity parameters.

Further, the drilling parameters include a drilling rate, a torque, a rotating speed, a drilling pressure and derived drilling specific work; the mechanical property parameters of the rock mass include uniaxial compressive strength, the Poisson's ratio, an internal friction angle, and modulus of elasticity; and the rock mass integrity parameter is represented by an RQD value.

The test purpose in the step 1) includes: A. establishing the relationship between the drilling parameters of the test piece and the mechanical properties of the rock mass under different confining pressures, and B. establishing the relationship between the rock mass integrity parameter RQD value and the drilling parameters;

the rock mass basic factors affecting the three-way confining pressure loading drilling in the step 1), for the purpose A, the basic factors are rock mass types, including granites, marbles, sandstones, shale and other rock masses of different types and from different origins; and for the purpose B, the basic factors are a rock fissure development degree and a fracture condition.

In the step 2), the relationship between the drilling parameters of the test piece and the mechanical properties of the rock mass under different confining pressures is tested, and the test piece can be a complete rock mass test piece or a fractured rock mass test piece;

the complete rock mass test piece is obtained by cutting and grinding different types of natural rocks according to the size requirements of the test piece of the multifunctional true triaxial rock drilling test system;

the complete rock mass test piece refers to a concrete or mortar test piece with different strength according to the size requirements of the test piece of the multifunctional true triaxial rock drilling test system;

the fractured rock mass test piece is obtained by respectively burying polyethylene pieces with different angles, different thicknesses and different distances in similar materials of the rock mass in advance according to the requirements of fracture parameters of the rock mass in the test solution, taking out the polyethylene pieces from the similar materials after primary solidification, demolding after the test piece is solidified and curing the test piece in a specific environment.

In the step 1), in view of the test of establishing the relationship between the rock mass integrity parameter RQD value and the drilling parameters, the test piece used is the fractured rock mass test piece, rock with a cross section of 300×300 mm and horizontal and smooth upper and lower surfaces and a sand or gravel layer are alternately placed in the pressure chamber and are circulated in several layers, and the height of each layer of rock and the sand or gravel layer can be varied according to the design of the test solution.

In the step 3), the rock core has a rock core diameter of 50 mm, after the drilling test is completed, the test piece is taken out, and then 3-4 drilling holes are drilled in the periphery of a test hole of the drilling rig, and the drilling hole serial number is k (k=1, 2, 3 . . . ).

In the step 4a), performing statistics on the core collection rate of the rock core of the test piece, and measuring the RQD value of the test piece includes: firstly performing statistics on the RQD value of each drilling hole, and then using the average value of the RQD value of each drilling hole as the RQD value of the test piece, and the RQD value of each drilling hole is the percentage of the ratio of the cumulative length of the rock core greater than 10 cm in the rock cores taken from each drilling hole to the drilling length of the drilling hole.

In the step 4b), the measurement of the mechanical property parameters of the test piece materials includes: cutting the rock core of each drilling hole into a standard test piece having a height of 100 mm, the standard test piece at the upper part to the test piece at the bottom end are sequentially marked as i, the depth of the ith standard test piece of the kth hole in the test piece is 100 (i−1) to 100i mm, and the standard test pieces having the same mark are grouped, for example, the ith standard test pieces of all holes belong to the ith group, and the uniaxial test and the triaxial test are performed on the ith group of standard test pieces to obtain the mechanical property parameters (uniaxial compressive strength $R_c$, cohesive force c, internal friction angle $\psi$, modulus of elasticity E) of the ith group to serve as the mechanical property parameters of test pieces at the depth of 100 (i−1) to 100i mm.

In the step 5), in view of the test of establishing the relationship between the rock mass integrity parameter RQD value and the drilling parameters, the collected data is preprocessed, the rotating speed r' and the torque m' sensitive to the fracture degree of the rock mass are processed to obtain a torque significant rate $\bar{\imath}$ and a rotating speed significant rate $\bar{r}$.

The torque significant rate $\bar{m}$ and a rotating speed significant rate $\bar{r}$ are as follows:

$$\bar{m}_k = |m_k' - m_{k+1}'|/m_k'$$

$$\bar{r}_k = |r_k' - r_{k+1}'|/r_k'$$

in which k represents the kth collection point of the data.

The critical value of the torque significant rate and the critical value of the rotating speed significant rate are obtained according to the test by using the same determination method, and the determination of the critical value of the torque significant rate is taken as an example. The critical value of the torque significant rate is determined according to the following method: recording a torque value when the fracture is encountered during the drilling process, calculating the torque significant rate $\bar{m}$, using all torque significant rates $\bar{m}$ when the fracture occurs in the drilling process as sample data, using the torque significant rates $\bar{m}$ corresponding to a confidence probability of 95% as a truncation probability of the sample parameters of the torque significant rate $\bar{m}$ according to a normal probability distribution model of the sample data, and determining the critical value of the torque significant rate.

In the step 5), in view of the test of establishing the relationship between the rock mass integrity parameter RQD value and the drilling parameters, establishing the relationship between the processed data and the rock mass integrity parameter RQD includes: on the basis of a large number of test data, performing formula fitting on the RQD value of the test piece, a torque fracture index $QD_m$ and a rotating speed fracture index $QD_r$ by using a multiple linear regression method, and the final form of the fitting formula is:

$$RQD = \beta_0 + \beta_1 QD_m + \beta_2 QD_r$$

in which $\beta_0$, $\beta_1$ and $\beta_2$ all represent regression coefficients.

The torque fracture index $QD_m$ and a rotating speed fracture index $QD_r$ are as follows:

$$QD_m = \frac{\sum h_i^1 + \sum l_j^1}{H}$$

$$QD_r = \frac{\sum h_i^2 + \sum l_j^2}{H}$$

In the formula, $h_i^1$ represents the length of the ith segment of which the torque significant rate $\bar{m}$ is less than the critical value in a certain drilling hole, and $l_i^1 l_j$ represents the length of the jth segment of which the torque significant rate index is greater than the critical value and the length is less than 100 mm. $h_i^2$ represents the length of the ith segment in which the rotating speed significant rate $\bar{m}$ is greater than the critical value, $l_j^2$ represents the length of the jth segment of which the rotating speed significant rate index is greater than the critical value and the length is less than 100 mm, and H represents the total length of a certain drilling hole.

In the step 5), in view of the test of establishing the relationship between the drilling parameters of the test piece and the mechanical properties of the rock mass under different confining pressures, preprocessing the collected data refers to segmenting the collected drilling rate v', the torque m', the rotating speed r', the drilling pressure n' of the test piece and the deduced drilling specific work w' data from the top to the bottom of the test piece at an interval of 100 mm, the ith segment represents that the depth of the test piece is 100 (i−1) to 100i mm, and an arithmetic mean value of the indexes of the segment is used as a representative value of the segment (the drilling rate v, the torque m, the rotating speed r, the drilling pressure n, and the deduced drilling specific work w).

In the step 5), establishing the relationship between the processed data and the same-depth rock mechanical properties includes: respectively performing regression on an optimal relational expression between the representative values of the drilling parameters and the mechanical property parameters of the rock in a stepwise regression method, including: fitting the optimal relational expression between the uniaxial compressive strength $R_c$ and the representative values of the drilling parameters, fitting the optimal relational expression between the cohesive force c and the representative values of the drilling parameters, fitting the optimal relational expression between the internal friction angle ψ and the representative values of the drilling parameters, and fitting the optimal relational expression between the modulus of elasticity E and the representative values of the drilling parameters. The fitting methods and operation steps of the four relational expressions are the same, and are illustrated by taking the fitting of the optimal relational expression between the internal friction angle ψ and the representative values of the drilling parameters as an example, and the following several steps are contained:

(1) defining independent variables and dependent variables, and calculating a correlation coefficient matrix, which includes 4 sub-steps.

A. the independent variables are the torque $x_1$, the rotating speed $x_2$, the drilling pressure $x_3$, the drilling rate $x_4$, and the drilling specific work $x_5$, the dependent variable is the internal friction angle $y_1$, and a 5-variable regression model is:

$$\hat{y_1} = b_0 + b_1 x_1 + b_2 x_2 + b_3 x_3 + b_4 x_4 + b_5 x_5$$

B. Calculating the Average Value of the Variables

For the independent variables and the dependent variables, there are n groups of data according to a large number of field tests, and then the average number of variables is:

$$\bar{x_i} = \frac{1}{n}\sum_1^n x_{ki}$$

$$\bar{y} = \frac{1}{n}\sum_1^n y_k$$

$X_{ki}$ represents the value of $x_i$ in the kth test data.

C. Calculating a Deviation Matrix

The sum of squares of the independent variables is $SS_i$, and the sum of products of the independent variables and the dependent variables are $SP_{ij}$ and $SP_{iy}$.

$$SS_i = \sum_1^n (x_{ki} - \bar{x_i})^2$$

$$SP_{ij} = \sum_1^n (x_{ki} - \bar{x_i})(x_{kj} - \bar{x_j})$$

$$SP_{iy} = \sum_1^n (x_{ki} - \bar{x_i})(y_k - \bar{y})$$

then a normal equation is obtained $$\begin{cases} SS_1 b_1 + SP_{12} b_2 + SP_{13} b_3 + S_{14} b_4 + SP_{15} b_5 = SP_{1y} \\ \ldots \\ SS_{51} b_1 + SP_{52} b_2 + SP_{53} b_3 + SP_{54} b_4 + SP_{55} b_5 = SP_{5y} \end{cases}$$

D. Calculating a Correlation Coefficient Matrix

In the stepwise regression, for ease of expression and calculation, the dispersion is usually transformed into a correlation matrix, and the calculation formula is:

$$r_{ij} = SP_{ij}/(SS_i SS_j)^{0.5}$$

in which, i,j=1, 2, 3, 4, 5, $r_{iy}$ represents the correlation coefficient of x1, x2, x3, x4, x5 and y; and the correlation coefficient matrix is:

$$\begin{cases} r_{11} p_1 + r_{12} p_2 + r_{13} p_3 + r_{14} p_4 + r_{15} p_5 = r_{1y} \\ \ldots \\ r_{51} p_1 + r_{52} p_2 + r_{53} p_3 + r_{54} p_4 + r_{55} p_5 = r_{5y} \end{cases}$$

then the correlation coefficient matrix is:

$$R^{(0)} = [r_{ij}^{(0)}]$$

In the formula, 0 represents the original correlation coefficient.

(2) Determining the F Test Standard of the Significance

The observation number n of the test sample is much greater than the number m of the independent variables, then the influence of the number m of the independent variables introduced on the degree of freedom of the remaining independent variables is small. At this time, a fixed F test value is selected without being replaced, the level of significance α should not be too small, for example, α=0.1. $F_α$ represents the F value when the level of significance is a, which can be obtained by searching for a test critical value table of F.

(3) Selecting the First Independent Variable

A. Calculating a Partial Regression Square Sum $u_i$ of 5 Independent Variables $$u_i = r_{iy}^2 / r_{ii} (i=1,2,3,4,5)$$

A greater $u_i$ value indicates greater contribution of the independent variable to the variance after the independent variable is introduced into the regression equation, the independent variable is introduced into the regression equation at first, for example, $x_k$ is introduced into the regression equation.

B. After the independent variable $x_k$ is introduced, the correlation coefficient matrix $R^{(l)}$ is changed by the following formula and is transformed into $R^{(l+1)}$.

$$\begin{cases} r_{kk}^{(l+1)} = 1/r_{kk}^{(l)} \\ r_{kj}^{(l+1)} = r_{kj}^{(l)}/r_{kk}^{(l)} \quad (j \neq k) \\ r_{ik}^{(l+1)} = -r_{ik}^{(l)}/r_{kk}^{(l)} \quad (i \neq k) \\ r_{ij}^{(l+1)} = r_{ij}^{(l)} - r_{ik}^{(l)}r_{kj}^{(l)}/r_{kk}^{(l)} \quad (i, j \neq k) \end{cases}$$

(4) Selecting the Second Independent Variable

A. Calculating the Regression Square Sum of the Independent Variables $$u_i^{(2)} = [r_{iy}^{(1)}]^2/r_{ii}^{(1)} (i=1,2,3,4,5)$$

Excluding the introduced $x_k$, the maximum independent variable in the independent variable $u_i^{(2)}u_i^{(2)}$ is introduced into the regression equation, for example, $x_l$.

B. performing F test on the introduced independent variable $x_l$.

$$F_l = u_5^{(2)}/[(1-u_k^{(1)}-u_l^{(2)})/(n-2-1)]$$

If $F_l > F_\alpha F_l > F_\alpha$, then $x_l$ is introduced, otherwise, $x_l$ is not introduced.

C. After $x_l$ is introduced, performing variation according to the formula $R^{(l+1)}$, and transforming $R^{(1)}$ into $R^{(2)}$.

D. performing a significance test on the introduced $x_k$ and $x_l$

First, the partial regression square sum and the remaining square sum are calculated.

$$u_i^{(3)} = [r_{iy}^{(2)}]^2/r_{ii}^{(2)} (i=1,2,3,4,5)$$

If $u_k^{(3)} > u_i^3 u_k^{(3)} > u_l^{(3)}$, $x_k$ and $x_l$ are significant and retained, or otherwise, $x_k$ is eliminated.

(5) Repeating the step (4) until all independent variables are extracted (6) Establishing an optimal regression equation In the stepwise regression analysis, the standardized quantity is used, that is, the solution $p_i$ obtained from the correlation coefficient is a standard regression coefficient, and then the standard regression coefficient is converted into a partial regression coefficient $b_i$, $$b_i = \frac{p_i S_y}{S_{xi}}$$

assuming that $x_k$, $x_l$ and $x_z$ are all selected independent variables, and $b_i$, $b_k$, $b_z$ are partial regression coefficients corresponding to the independent variables;

$$b_0 = \overline{y}_1 - b_l \overline{x}_l - b_k \overline{x}_k - b_z \overline{x}_z$$

The optimal regression equation is:

$$\widehat{y_1} = b_0 + b_k x_k + b_l x_l + b_z x_z.$$

The drilling test in the step 3) using the true triaxial rock drilling tester includes the following steps:

Step A: the test piece is placed on a test piece platform in the pressure chamber composed of the lateral loading plates for applying the confining pressure, and then the pressure chamber is pushed into the center of a test bench.

Step B: a set confining pressure value is input to computer software matched with the logic controller, the logic controller controls the hydraulic pump station to work, hydraulic oil enters the four lateral hydraulic oil cylinders and pushes the lateral loading plates to apply a lateral pressure to the test piece, and the lateral confining pressure sensor receives a pressure signal of the lateral hydraulic oil cylinders at all times and dynamically maintains the confining pressure together with the logic controller.

Step C: a set axial pressure value is input in the software, the axial hydraulic oil cylinder drives the axial loading plate to lift the pressure chamber, so that the test piece contacts the platform plate at the bottom of the top reaction force frame and squeezes each other to generate an axial force function, and the axial pressure sensor dynamically maintains the axial pressure together with the logic controller.

Step D: the operating parameters of the core collection drilling rig are set in the software, the logic controller controls the servo motor of the hydraulic pump station and the drilling rig servo motor, and then controls the drilling rig top hydraulic oil cylinder to push the drilling rig unit to move downward so as to continue drilling, the drilling rig displacement sensor and the rotating speed sensor monitor the drilling rate and the rotating speed in the drilling process at all times, and cooperate with the logic controller, the servo motor and the speed reducer in the drilling rig to make the drilling rig work under the set parameters until the drilling is completed.

The third solution provided by the present invention is as follows:

A method for evaluating an anchoring and grouting reinforcement effect based on drilling parameters is provided, including: performing an indoor drilling test on the rock test piece obtained onsite before and after anchoring and grouting reinforcement based on the above multifunctional true triaxial rock drilling test system, designing an anchoring and grouting reinforcement solution according to the representative value of the equivalent uniaxial compressive strength of the test piece before the anchoring and grouting reinforcement, and judging the reasonableness of the anchoring and grouting reinforcement solution via a guarantee rate λ of the equivalent uniaxial compressive strength after the test piece is reinforced.

A method for evaluating an anchoring and grouting reinforcement effect based on drilling parameters includes the following specific steps:

Step A): taking onsite fractured rocks in an underground engineering, manufacturing indoor drilling test pieces, and dividing the indoor drilling test pieces into several groups;

step B): taking any group as an example, randomly taking a part of test pieces, implementing an indoor drilling test, recording the drilling parameters of three test pieces, substituting the drilling parameters of each test piece into the optimal regression relational expression of the uniaxial compressive strength and the drilling parameters in the step 5) in the second solution to obtain the equivalent uniaxial compressive strength of each test piece, and then obtaining a representative value of the equivalent uniaxial compressive strength of the group of fractured rock masses; step C): comparing the representative value of the equivalent uniaxial compressive strength obtained in the step B) with an expected strength value, designing an anchoring and grouting solution, implementing the same anchoring and grouting reinforcement solution on the rest test pieces in the group, and curing the test pieces under the same conditions;

step D): performing the indoor drilling test on the cured reinforced test piece, and substituting the drilling parameters into the optimal regression relational expression of the uniaxial compressive strength and the drilling parameters in the step 5) to obtain the equivalent uniaxial compressive strength of each test piece;

step E): calculating a guarantee rate of the equivalent uniaxial compressive strength after the reinforcement of the group of test pieces, if the guarantee rate is greater than 95%, judging that the grouting reinforcement solution is reasonable, or otherwise, judging that the grouting reinforcement solution is unreasonable.

Further, the calculation method of the equivalent compressive strength of the test piece in the step C) includes: substituting the drilling parameters, including the torque m, the rotating speed r, the drilling pressure n and the drilling specific work w of the drilling rig into the optimal regression relational expression of the uniaxial compressive strength and the drilling parameters in the step 5) in the second solution to obtain the equivalent uniaxial compressive strength of each test piece.

Further, the representative value of the equivalent uniaxial compressive strength of the fractured rock mass is represented by the average value of the equivalent compressive strengths of part of test pieces; if the deviation between the maximum value and the average value or between the minimum value and the average value is greater than 15%, an intermediate value is used as the representative value, and if the deviations between the maximum value and the average value and the deviations between the minimum value and the average value are both greater than 15%, the group of data is invalid.

Further, the anchoring and grouting reinforcement solution is to determine a slurry-water-cement ratio, a grouting pressure, an anchor rod length and an anchor rod diameter.

Further, the calculation method of the guarantee rate of the equivalent uniaxial compressive strength is:

$$\lambda = \frac{num}{N} \times 100\%$$

in which num represents the number of reinforced test pieces with equivalent uniaxial compressive strength greater than the expected strength value in the group, and N represents the total number of the reinforced test pieces in the group.

The beneficial effects of the present invention are as follows:

(1) The multifunctional true triaxial rock drilling test system provided by the present invention can impart a three-way pressure to the test piece, and truly simulate the stress state of the rock in the underground engineering and the drilling working environment.

(2) The multifunctional true triaxial rock drilling test system of the present invention also has the functions of a single shaft and a rock mass true triaxial press machine, and can also continuously heat the test piece by using a special steel heating plate, further perform a research on the mechanical properties of the test piece and the influence on the drilling parameters under the action of thermal coupling, and perform a research on the mechanical properties of the rock mass under the action of thermal coupling. In addition, the water-containing rock mass can be placed in the rubber box so that the tester can test the water-containing rock mass, and the test system has a multifunctional feature.

(3) According to the method for evaluating the anchoring and grouting reinforcement effect based on drilling parameters provided by the present invention, the equivalent compressive strength index is introduced to avoid the problem that the mechanical parameters of the fractured rock mass cannot be tested before the anchoring and grouting reinforcement to result in that the anchoring and grouting reinforcement effect cannot be quantitatively evaluated.

(4) According to the method for evaluating the anchoring and grouting reinforcement effect based on drilling parameters provided by the present invention, rapid quantitative evaluation is performed on the anchoring and grouting reinforcement effect to quickly judge the rationality of the anchoring and grouting reinforcement effect so as to adjust the anchoring and grouting solution in time, therefore the method has realistic scientific research and engineering significance.

(5) By adoption of the multifunctional true triaxial rock drilling tester and the test method proposed by the present invention, the drilling parameters, the mechanical properties of the rock mass and the fracture boundary conditions are established to replace the step of onsite core collection for indoor test, thereby not only reducing the time from the onsite core collection to the acquisition of a test report, but also avoiding the problem that the collected rock core has been removed from the original environmental stress, temperature and other constraint conditions, such that the rock core cannot well represent the strength of the rock mass, and the problem that the rock core collection rate and integrity are difficult to guarantee during drilling in weak and fractured complex stratum so that the physical properties and mechanical parameters of the local rock stratum cannot be obtained is solved, and then, the measured surrounding rock strength is more scientific and reliable.

(6) The drilling test system provided by the present invention can measure the displacement, the drilling rate, the rotating speed and torque parameters in the drilling process of the drilling rig, and can set the drilling rate and the rotating speed or set the drilling rate and the torque to achieve constant displacement drilling, and can also set the drilling pressure and the rotating speed or set the drilling pressure and the torque to achieve constant pressure drilling.

REFERENCE SIGNS

1, main frame upper upright post; 2, top reaction force frame; 3, platform plate; 4, main frame lower upright post; 5, pressure chamber; 6, test piece; 7, lateral loading plate; 8, positioning ball; 9, wheel; 10, axial loading plate; 11, axial hydraulic oil cylinder; 12, inner piston rod of axial hydraulic oil cylinder; 13, main frame bottom platform; 14, guide rail base; 15, drilling rig fixing plate; 16, drilling rig servo motor; 17, speed reducer; 18, belt transmission device; 19, drill pipe; 20, torque sensor; 21, lateral hydraulic oil cylinder; 22, lateral piston rod; 23, test piece cushion block; 24, pressure chamber rail; 25, drilling rig top hydraulic oil cylinder; 26, lateral reaction force plate; 27, lateral rib of pressure chamber, 28, bottom plate of pressure chamber; 29, logic controller; 30 heating plate; 31, pipeline inlet; 32, pipeline; 33, pipeline outlet.

DETAILED DESCRIPTION OF THE EMBODIMENTS

The technical solutions in the embodiments of the present invention will be clearly and completely described below with reference to the drawings.

Figure 1:
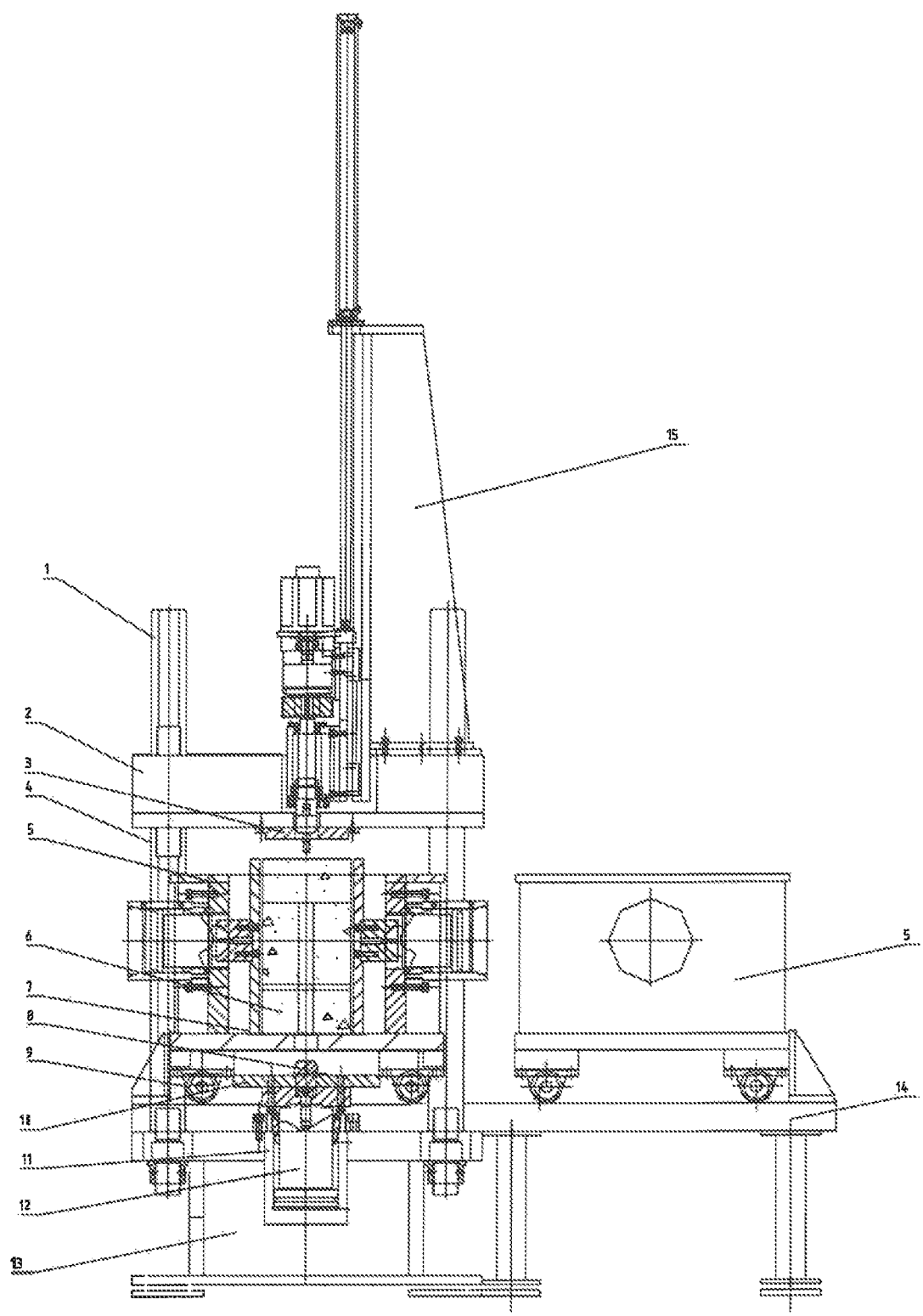
FIG. 1 is a schematic diagram of a front structure of a multifunctional true triaxial rock drilling test system according to the present invention.
Figure 2:
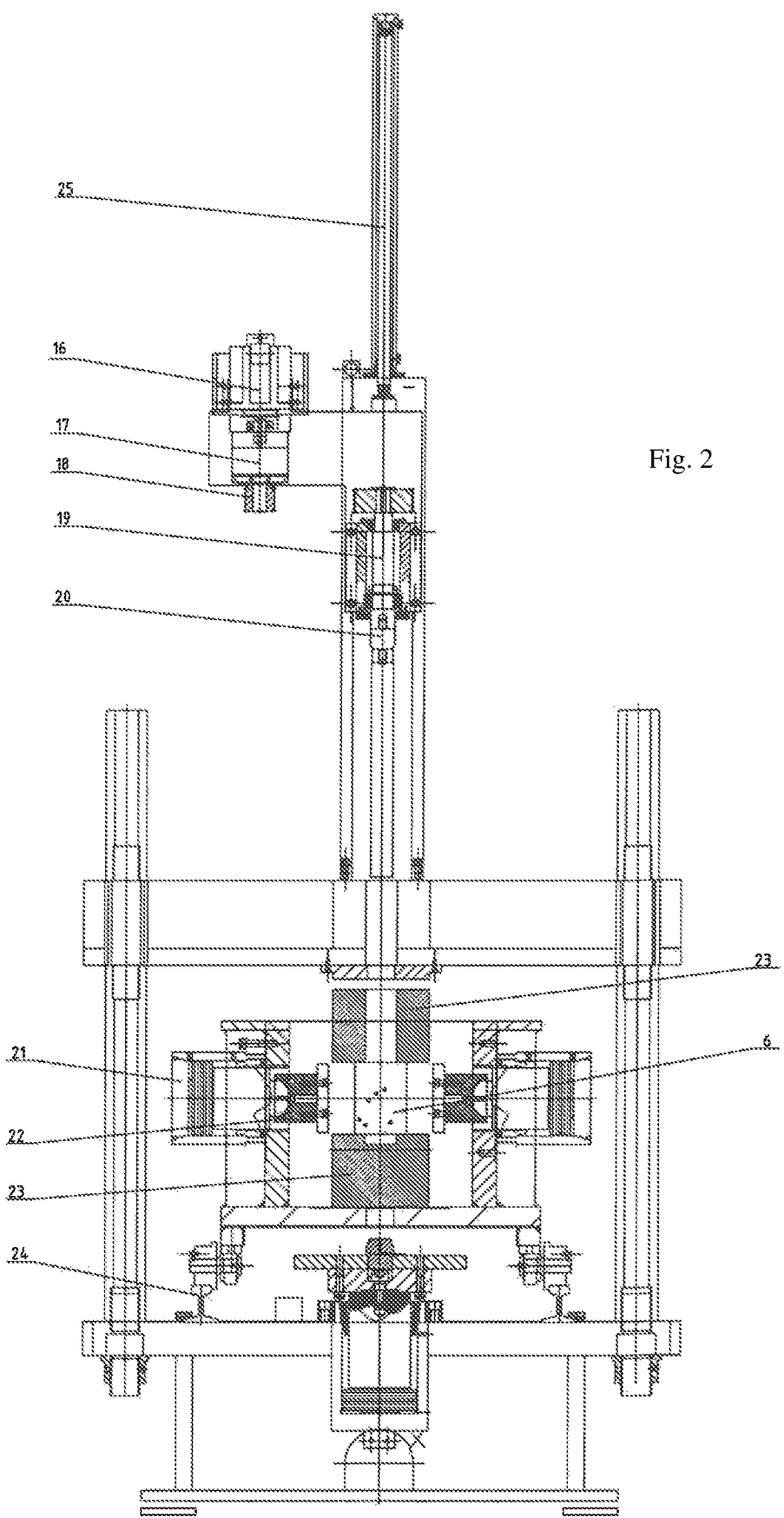
FIG. 2 is a schematic diagram of a side structure of the multifunctional true triaxial rock drilling test system according to the present invention.
Figure 3:
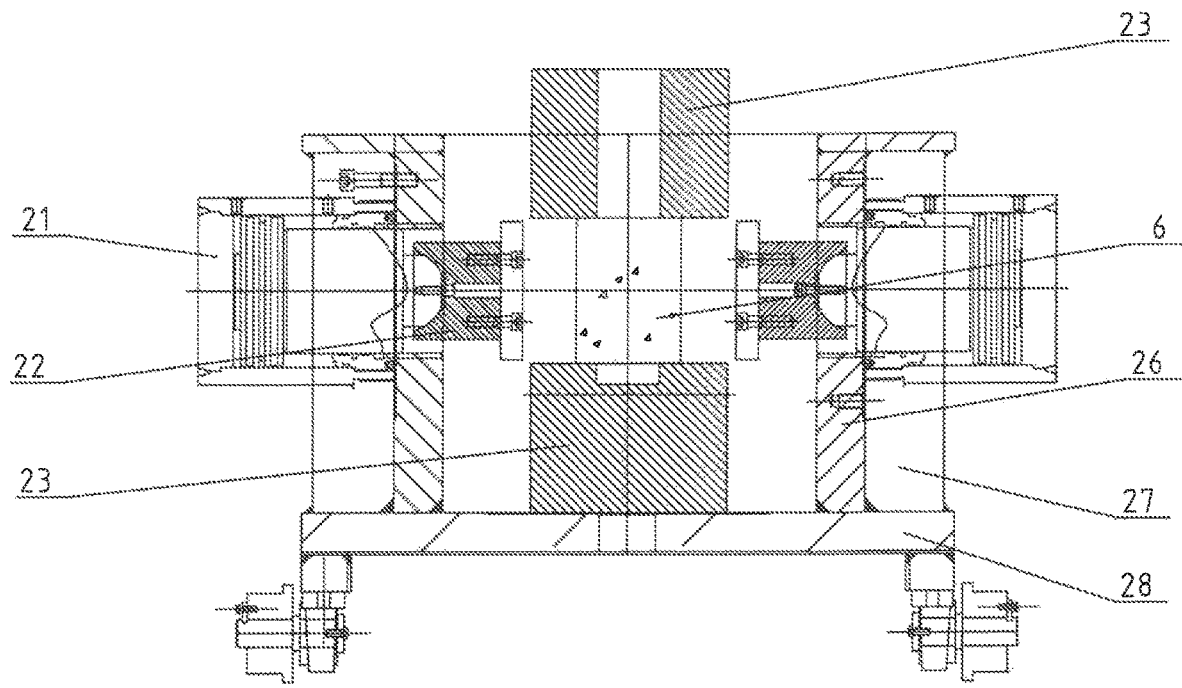
FIG. 3 is a schematic diagram of sections of a confining pressure application device and a pressure chamber in the device according to the present invention.
Figure 4:
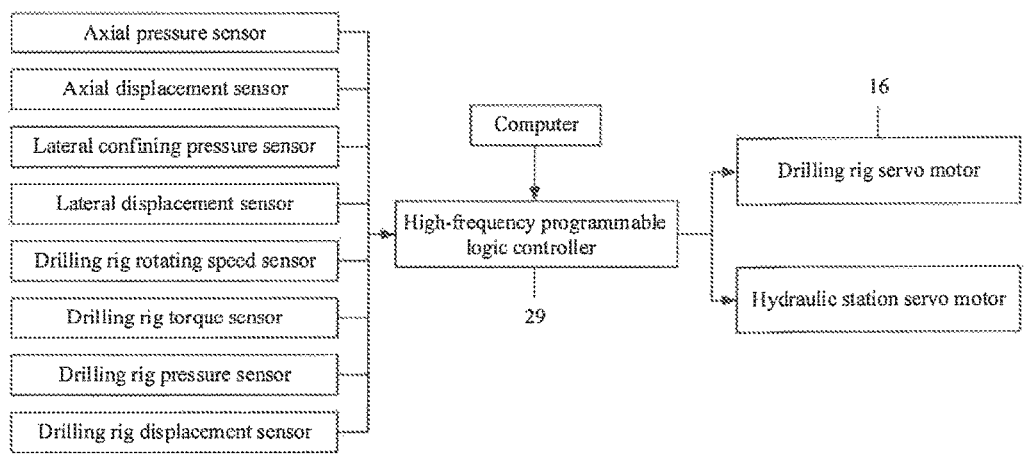
FIG. 4 is a schematic block diagram of a monitoring control system in the device according to the present invention.

As shown in FIG. 1 and FIG. 2, a multifunctional true triaxial rock drilling test system includes a supporting frame with a reaction force frame at the top, a pressure chamber is arranged in the supporting frame, a test piece platform for placing a test piece is arranged in the pressure chamber, a surrounding rock loading device is arranged on the side of the pressure chamber, an axial pressure loading device for contact between the upper part of the test piece and the reaction force frame is arranged at the bottom of the pressure chamber, a drilling rig unit capable of lifting and rotating is arranged at the upper part of the reaction force frame, and the drilling tester further includes a sensor for measuring drilling parameters of the test piece, and a monitoring control system connected with the sensor.

The sensor includes an axial displacement sensor arranged at the bottom of the test piece platform, a drilling rig rotating speed sensor and a drilling rig torque sensor arranged on the drilling rig, and a lateral confining pressure sensor and a lateral displacement sensor arranged on the surrounding rock loading device.

The bottom of the supporting frame is supported on the test bench or on the ground. A cylindrical concave hole is formed in the middle of a main frame bottom platform 13, an axial hydraulic oil cylinder 11 is placed in the concave hole, a piston rod protrudes from the top of the axial hydraulic oil cylinder, the piston rod is fixedly connected to an axial loading plate 10, the piston rod and the test bench are sealed by a sealing plug, a test piece 6 is placed on the test piece platform, a top reaction force frame 2 is arranged at the top of the test piece 6, and the top reaction force frame 2 is supported by a main frame upper upright post 1 and a main frame lower upright post 4.

The working principle of the axial loading device is as follows: a hydraulic pump pushes hydraulic oil into the axial hydraulic oil cylinder 11 to push the piston rod 12 in the axial hydraulic oil cylinder to move upward, and after moving upward for a distance, the axial loading plate 10 pushes the test piece 6 to move upward and contact the top reaction force frame 2 to apply a force. The piston rod is a variable-section piston rod having a circular cross section at the bottom, and the cross section of the circular piston rod is increased for several times from bottom to top, and the top of the piston rod is fixedly connected with a square steel axial loading plate 10.

The bottom of the pressure chamber is spaced apart from a pressure chamber rail 24 with a set distance, and the axial loading plate 10 is arranged at the upper part of the rail, and the pressure chamber is slidable on the rail.

A platform plate 3 is fixedly connected to the lower part of the top reaction force frame, and is directly in contact with the test piece 6, and reserved holes are formed in the middles of the platform plate 3 and the reaction force frame to allow passage of the drill pipe of the drilling rig.

With respect to the confining pressure loading device, the test piece 6 is provided with a lateral hydraulic oil cylinder 21 on each side face, the lateral hydraulic oil cylinder 21 extends out from a lateral piston rod, the lateral piston rod 22 is fixedly connected to a lateral loading plate 7, the end part of the lateral hydraulic oil cylinder is embedded in a lateral reaction force plate 26 to provide a supporting reaction force for the lateral hydraulic oil cylinder 21, and a lateral rib 27 of the pressure chamber is arranged on one side of the lateral reaction force plate 26, the confining pressure loading device is placed on the test piece platform, can move up and down with the test piece platform and is pulled out along the rail, the lateral hydraulic oil cylinder adjacent to the confining pressure loading device can be independently controlled, that is, unequal pressures can be applied to the side faces of the adjacent test pieces 6.

The lateral loading plate 7 is a rectangular steel plate, which applies a horizontal pressure to the test piece under the push of the piston driven by the hydraulic oil cylinder, the height of the loading plate is the same as that of the test piece 6, and the width is slightly smaller than that of the test piece 6 to prevent mutual interference of the adjacent lateral loading plates 7 after the test piece is compressed and deformed.

A drilling rig slide rail is a drilling rig top hydraulic oil cylinder 25 arranged at the top of the reaction force frame through a drilling rig fixing plate 15, the drilling rig can move up and down along the drilling rig slide rail, the drilling rig is fixedly connected with a drilling rig servo motor 16 and move upward or downward under the push or pull of the piston at the top of the drilling rig in the hydraulic oil cylinder of the upper drilling rig, the drilling rig servo motor 16 provides a rotating force for the drilling rig, the drilling rig top hydraulic oil cylinder 25 provides a downward pressure for the drilling rig, the drill pipe of a drilling bit of the drilling rig is in contact with the test piece through the reserved holes of the reaction force frame 2 at the top of the test piece and the loading plate for drilling, the main shaft of the drilling rig servo motor 16 is inserted into a speed reducer 17, a belt transmission device is arranged between the main shaft and a drill pipe 19, the belt transmission device is connected with the speed reducer at one end through a gear, and is connected with the main shaft of the servo motor at the other end, the belt transmission device and the speed reducer constitute a two-stage speed reduction mechanism, and the reduction multiples is changed with the diameter ratio of the gears at both ends of the belt.

The drilling rig can be arranged as a rotary cutting drilling rig or an impact drilling rig. The drilling bit of the rotary cutting drilling rig can be arranged as a core collection drilling bit and can also be set as a non-core collection drilling bit.

The monitoring control system consists of an axial pressure sensor, an axial displacement sensor, four lateral confining pressure sensors, four lateral displacement sensors, a drilling rig rotating speed sensor, a drilling rig torque sensor 20, a drilling rig pressure sensor, a drilling rig displacement sensor, a logic controller 29, a power amplifier and a servo motor.

The monitoring control system can control the axial pressure and the confining pressure, and can also control either of two groups of values of the drilling rig, namely the torque and the rotating speed, and the drilling pressure and the displacement.

The working process is as follows: the logic controller accepts signals of the respective sensors, compares the signals with set values, and issues a voltage instruction to control the servo motor to work via the power amplifier and realize closed loop control.

The present invention has the function of a uniaxial test machine. A uniaxial test piece is placed in the pressure chamber 5, steel cushion blocks 23 are placed on and below the uniaxial test piece, the axial loading device lifts the pressure chamber 5, so that the steel cushion blocks 23 on the uniaxial test piece are in contact with the platform plate 3 below the reaction force frame 2, the uniaxial test piece is in a uniaxial compression state, the axial load loading device is controlled to be in a constant strain loading mode, and the axial pressure is applied to the test piece at a loading speed suggested by the International Society for Rock Mechanics until the test piece is broken.

The multifunctional true triaxial rock drilling test system can perform constant pressure incremental loading by using the axial pressure loading device and the confining pressure loading device, can realize the independent application of three main stresses of the rock mass test piece, and has a part of functions of a rock mass true triaxial test machine.

In the case that the test piece contains water therein or is filled with fracture water, the test piece can be placed in a high-pressure sealing rubber box having an inner size being consistent with the size of the test piece, the top of the test piece may be covered with a rubber cover slightly larger than the bottom rubber box, a pore is reserved in the area of the rubber cover through which the drilling bit and the drill pipe of the drilling rig penetrate, the axial and lateral loading plates apply the pressure to the rubber box and the rubber cover, and a three-way pressure is applied to the test piece through the rubber box and the rubber cover. This design can prevent the internal water from flowing outside, so that the tester can test the water-containing rock mass.

Figure 5:
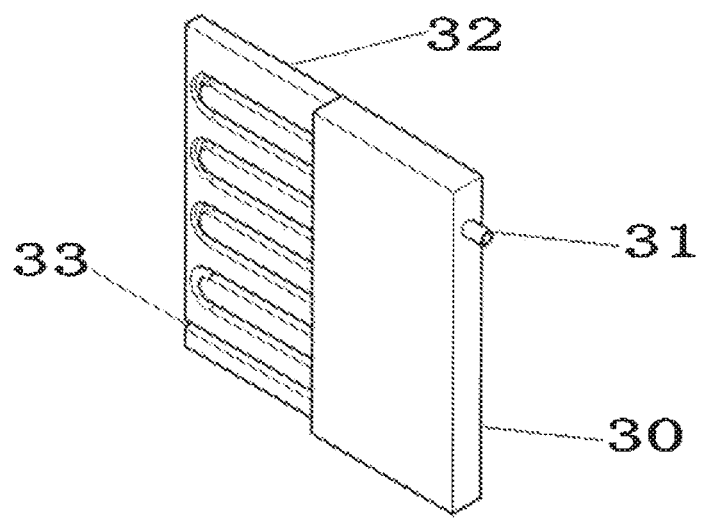
FIG. 5 is a structural schematic diagram of a heating plate in the device according to the present invention.

At the outside of the test piece 6, as shown in FIG. 5, a special steel heating plate 30 is placed on the inner side of the lateral loading plate 7, the thickness of the heating plate 30 is greater than 20 mm, a curved pipeline 32 is arranged in the heating plate 30, a pipeline inlet 31 is welded on one side face of the top heating plate, a pipeline outlet 33 is welded on the lower end of an opposite side face, so that water vapor or high temperature liquid passes through the pipeline to heat the test piece, and then the mechanical properties of the test piece under thermal coupling are studied.

Embodiment 1

In the device of the embodiment, it is taken as an example that the drilling bit used in a drilling rig module is a core collection drilling bit, and in addition, a non-core collection drilling bit can also be selected.

First step: the test piece 6 is manufactured, the pressure chamber 5 is pulled out to the end part of a guide rail base 14 along the pressure chamber rail 24, the test piece 6 is placed at the central position of the pressure chamber 5, and then the pressure chamber 5 is pushed into the other end of the pressure chamber rail 24.

Second step: a set axial pressure value is input in a control module, the logic controller controls the servo motor of a hydraulic station to drive the hydraulic pump to provide power for the axial hydraulic oil cylinder 11, the axial loading plate 10 moves up and down under the push of the piston rod 12 of the axial hydraulic oil cylinder, so that a positioning ball 8 ascends to enter a positioning hole reserved in the center of a bottom plate 28 of the pressure chamber to complete the positioning work, the axial loading plate 10 lifts the pressure chamber 5, so that the test piece 6 or the cushion block 23 at the upper part of the test piece contact with the platform plate 3 at the bottom of the main frame reaction force frame 2 to press against each other to generate an axial force, and the axial pressure sensor receives pressure signals of the axial hydraulic oil cylinder 11 at all times, transmits the pressure signals to the logic controller 29, and compares the pressure signals with a set value to dynamically maintain the axial pressure.

Third step: a set confining pressure value is input in the control module, the logic controller 29 controls the servo motor of the hydraulic station to drive the hydraulic pump to provide force for the lateral hydraulic oil cylinder 21, thereby pushing the lateral loading plate 7 to pressurize the side of the test piece 6, and the lateral confining pressure sensor receives the pressure signals of the lateral hydraulic oil cylinder 21 at all times, transmits the pressure signals to the logic controller 29, and compares the pressure signals with the set value to dynamically maintain the confining pressure.

Fourth step: operating parameters of the drilling rig unit, such as the drilling rate and the rotating speed of the drilling rig, are set in the software, and the logic controller 29 controls the drilling rig servo motor 16 to rotate the drilling rig at a preset rotating speed, the logic controller 29 controls the servo motor of the hydraulic pump station to provide hydraulic power for the drilling rig top hydraulic oil cylinder 25, so as to push the drilling rig unit to move downward, the drilling bit and the drill pipe penetrate through the reserved holes in the main frame reaction force frame 2 and the platform plate 3 at the top of the test piece to contact the test piece 6 for continuous drilling, the drilling rig displacement sensor and the rotating speed sensor constantly monitor the drilling rate and the rotating speed in the drilling process of the drilling rig and transmit the drilling rate and the rotating speed to the control module so as to dynamically maintain a constant drilling rate and rotating speed, and the drilling rig torque and the drilling pressure of the drilling rig are measured and are recorded in the logic controller until the test piece is drilled through.

Fifth step: after the fourth step is completed, the rock core is taken out from the core collection drill pipe, and is cut and polished to manufacture a standard rock test piece.

Sixth step: the confining pressure of the test piece 6 is released, the pressure chamber 5 is lowered onto the pressure chamber rail 24, the pressure chamber 5 is pulled out to the end part of the guide rail base 14 along the pressure chamber rail 24, the standard rock test piece obtained in the fifth step and the corresponding cushion blocks are placed at the center of the pressure chamber 5, and then the pressure chamber 5 is pushed into the other end of the pressure chamber rail 24.

Seventh step: the constant pressure incremental loading of the axial loading device is set by the control module, so that the pressure increases of the hydraulic oil cylinders within a unit time are the same, the axial loading plate 10 lifts the pressure chamber 5, the cushion block at the upper part of the standard rock test piece contacts the platform plates 3 at the bottom of the main frame reaction force frame 2 to press against each other to generate the axial force, the axial force is increased according to a uniaxial test pressure increment value recommended by the International Society for Rock Mechanics, the strain value and the pressure value during the loading process are monitored until the test piece is broken, and then the uniaxial compression test is completed.

Eighth step: a core is taken from the rock in the same batch as the test piece 6, the standard rock test piece is manufactured, and an indoor triaxial compression test is executed to obtain the modulus of elasticity, the cohesive force and the internal friction angle of this batch of rock samples.

Ninth step: correlation analysis is performed on the torque and pressure data of the drilling rig module of the test piece 6 measured in the drilling process and the uniaxial compressive strength, the modulus of elasticity, the cohesive force and the internal friction angle of the standard test piece to obtain the relationship between the drilling parameters and mechanical parameters (uniaxial compressive strength, modulus of elasticity, internal friction angle, cohesive force) of different rock masses under the three-way confining pressure.

The following control modes can be achieved in the entire process:

The drilling rig is controlled in four modes:

A. controlling a torque and a drilling rate, and collecting a drilling pressure and a rotating speed;

B. controlling the torque and the drilling pressure, and collecting a rotating speed and a drilling rate;

C. controlling the rotating speed and the drilling rate, and collecting the torque and the drilling pressure;

D. controlling the rotating speed and the drilling pressure, and collecting the torque and the drilling rate.

The axial pressure and the confining pressure of the test piece are controlled in three modes:

A. a constant strain loading mode, in which small strains occurring in the test piece within a unit time are the same;

B. a constant pressure incremental loading mode, in which the pressure increase of the hydraulic oil cylinder within the unit time is the same;

C. a constant force maintenance mode, in which the test piece is kept at a set confining pressure value.

Embodiment 2

A test method for characterizing rock mass characteristics by using drilling parameters in underground engineering is provided. The test purpose of establishing the relationship between drilling parameters of a test piece under different confining pressures and the mechanical properties of the rock mass is taken an example, the specific steps are as follows:

Step 1) according to the test purpose, rock mass basic factors affecting the three-way confining pressure loading drilling are determined, that is, different types of rock mass tests are prepared, such as granite, marble, limestone, transparent similar materials, concrete blocks with different strength and other rock types.

Step 2) a corresponding test piece is prepared according to the test solution, and the different types of rock masses are cut into rectangles with cross sections of 300×300 mm and height of 300-600 mm.

Step 3) a three-way confining pressure drilling test is performed on the prepared test piece, the drilling parameters in the drilling process of the test piece are collected during the test, and the rock core of the test piece is obtained, wherein the specific operation steps of the three-way confining pressure drilling test are shown in the embodiment 1.

Step 4), after the drilling test is completed, 3-4 drilling holes are drilled in the periphery of a test hole by using a core collection drilling rig, and the drilling hole serial number is k (k=1, 2, 3 . . . ), the rock core of each drilling hole is cut into a standard test piece having a height of 100 mm, the standard test piece at the upper part to the standard test piece at the bottom end are sequentially marked as i, the depth of the ith standard test piece of the kth hole in the test piece is 100 (i−1) to 100i mm, and the standard test pieces having the same mark are grouped, for example, the ith standard test piece of all holes belongs to the ith group, and the uniaxial test and the triaxial test are performed on the ith group of standard test piece to obtain the mechanical property parameters (uniaxial compressive strength $R_c$, cohesive force c, internal friction angle $\psi$, modulus of elasticity E) of the ith group to serve as the mechanical property parameters of test pieces at the depth of 100 (i−1) to 100i mm.

Step 5), the collected data is preprocessed, that is, the collected drilling rate v', the torque m', the rotating speed r', the drilling pressure n' of the test piece and the deduced drilling specific work w' data from the top to the bottom of the test piece at an interval of 100 mm, the ith segment represents that the depth of the test piece is 100 (i−1) to 100i mm, and an arithmetic mean value of the indexes of the segment is used as a representative value of the segment (the drilling rate v, the torque m, the rotating speed r, the drilling pressure n, and the deduced drilling specific work w).

Step 6, regression is respectively performed on an optimal relational expression between the representative values of the drilling parameters and the mechanical property parameters of the rock in a stepwise regression method, including: fitting the optimal relational expression between the uniaxial compressive strength $R_c$ and the representative values of the drilling parameters, fitting the optimal relational expression between the cohesive force c and the representative values of the drilling parameters, fitting the optimal relational expression between the internal friction angle $\psi$ and the representative values of the drilling parameters, and fitting the optimal relational expression between the modulus of elasticity E and the representative values of the drilling parameters. The fitting methods and operation steps of the four relational expressions are the same, and are illustrated by taking the fitting of the optimal relational expression between the internal friction angle $\psi$ and the representative values of the drilling parameters as an example, and the following several steps are contained:

(1) defining independent variables and dependent variables, and calculating a correlation coefficient matrix, which includes 4 steps.

A. the independent variables are the torque $x_1$, the rotating speed $x_2$, the drilling pressure $x_3$, the drilling rate $x_4$, and the drilling specific work $x_5$, the dependent variable is the internal friction angle $y_1$, and a 5-variable regression model is:

$$\hat{y}_1 = b_0 + b_1 x_1 + b_2 x_2 + b_3 x_3 + b_4 x_4 + b_5 x_5$$

B. Calculating the Average Value of the Variables

For the independent variables and the dependent variables, there are n groups of data according to a large number of field tests, and then the average number of variables is:

$$\bar{x}_i = \frac{1}{n} \sum_{1}^{n} x_{ki}$$

$$\bar{y} = \frac{1}{n} \sum_{i}^{n} y_k$$

$X_{ki}$ represents the value of $x_i$ in the kth test data.

C. Calculating a Deviation Matrix

The sum of squares of the independent variables is $SS_i$, and the sum of products of the independent variables and the dependent variables are $SP_{ij}$ and $SP_{iy}$ $$SS_i = \sum_1^n (x_{ki} - \overline{x_i})^2$$

$$SP_{ij} = \sum_1^n (x_{ki} - \overline{x_i})(x_{kj} - \overline{x_j})$$

$$SP_{iy} = \sum_1^n (x_{ki} - \overline{x_i})(y_k - \overline{y})$$

then a normal equation is obtained $$\begin{cases} SS_1 b_1 + SP_{12}b_2 + SP_{13}b_3 + S_{14}b_4 + SP_{15}b_5 = SP_{1y} \\ \ldots \\ SS_{51}b_1 + SP_{52}b_2 + SP_{53}b_3 + SP_{54}b_4 + SP_{55}b_5 = SP_{5y} \end{cases}$$

D. Calculating a Correlation Coefficient Matrix

In the stepwise regression, for ease of expression and calculation, the dispersion is usually transformed into a correlation matrix, and the calculation formula is:

$$r_{iy} = SP_{ij}/(SS_i SS_j)^{0.5}$$

In the formula, i, j=1, 2, 3, 4, 5, $r_{iy}$ represents the correlation coefficient among $x_1$, $x_2$, $x_3$, $x_4$, $x_5$ and y; and the correlation coefficient matrix is:

$$\begin{cases} r_{11}p_1 + r_{12}p_2 + r_{13}p_3 + r_{14}p_4 + r_{15}p_5 = r_{1y} \\ \ldots \\ r_{51}p_1 + r_{52}p_2 + r_{53}p_3 + r_{54}p_4 + r_{55}p_5 = r_{5y} \end{cases}$$

then the correlation coefficient matrix is:

$$R^{(0)} = [r_{ij}^{(0)}]$$

in which, 0 represents the original correlation coefficient.

(2) Determining the F Test Standard of the Significance

The observation number n of the test sample is much greater than the number m of the independent variables, then the influence of the number m of the independent variables introduced on the degree of freedom of the remaining independent variables is small. At this time, a fixed F test value is selected without being replaced, the level of significance α should not be too small, for example, α=0.1. $F_\alpha$ represents the F value when the level of significance is a, which can be obtained by searching for a critical value table of F test.

(3) Selecting the First Independent Variable

A. calculating a partial regression square sum $u_i$ of 5 independent variables $$u_i = r_{iy}^2 / r_{ii} (i = 1, 2, 3, 4, 5)$$

A greater $u_i$ value indicates greater contribution of the independent variable to the variance after the independent variable is introduced into the regression equation, the independent variable is introduced into the regression equation at first, for example, $x_k$ is introduced into the regression equation.

B. After the independent variable $x_k$ is introduced, the correlation coefficient matrix $R^{(l)}$ is changed by the following formula and is transformed into $R^{(l+1)}$.

$$\begin{cases} r_{kk}^{(l+1)} = 1/r_{kk}^{(l)} \\ r_{kj}^{(l+1)} = r_{kj}^{(l)}/r_{kk}^{(l)} \ (j \neq k) \\ r_{ik}^{(l+1)} = -r_{ik}^{(l)}/r_{kk}^{(l)} \ (i \neq k) \\ r_{ij}^{(l+1)} = r_{ij}^{(l)} - r_{ik}^{(l)} r_{kj}^{(l)}/r_{kk}^{(l)} \ (i, j \neq k) \end{cases}$$

(4) Selecting the Second Independent Variable

A. Calculating the Regression Square Sum of the Independent Variables $$u_i^{(2)} = [r_{iy}^{(1)}]^2 / r_{ii}^{(1)} (i = 1, 2, 3, 4, 5)$$

Excluding the introduced $x_k$, the maximum independent variable in the independent variable $u_i^{(2)} u_i^{(2)}$ is introduced into the regression equation, for example, $x_l$.

B. Performing F Test on the Introduced Independent Variable $x_l$.

$$F_i = u_S^{(2)} / [(1 - u_k^{(1)} - u_l^{(2)}) / (n - 2 - 1)]$$

If $F_i > F_\alpha F_i > F_\alpha$, then the $x_l$ is introduced, otherwise, $x_l$ is not introduced.

C. After $x_l$ is introduced, performing variation according to the formula $R^{(l+1)}$, and transforming $R^{(1)}$ into $R^{(2)}$.

D. Performing a Significance Test on the Introduced $x_k$ and $x_l$ firstly the partial regression square sum and the remaining square sum are calculated $$u_i^{(3)} = [r_{iy}^{(2)}]^2 / r_{ii}^{(2)} (i = 1, 2, 3, 4, 5)$$

If $u_k^{(3)} > u_l^3 u_k^{(3)} > u_l^{(3)}$, $x_k$ and $x_l$ are significant and retained, or otherwise, $x_k$ is eliminated.

(5) Repeating the step (4) until all independent variables are extracted (6) Establishing an optimal regression equation In the stepwise regression analysis, the standardized quantity is used, that is, the solution $p_i$ obtained from the correlation coefficient is a standard regression coefficient, and then the standard regression coefficient is converted into the partial regression coefficient $b_i$, $$b_i = \frac{p_i S_y}{S_{xi}}$$

assuming that xk, xl and xz are all selected independent variables, and $b_l$, $b_k$ and $b_z$ are partial regression coefficients corresponding to the independent variables;

$$b_0 = \overline{y_1} - b_l \overline{x_l} - b_k \overline{x_k} - b_z \overline{x_z}$$

The optimal regression equation is:

$$\widehat{y_1} = b_0 + b_k x_k + b_l x_l + b_z x_z.$$

By means of the above calculation method, the relational expression characterizing the rock mass characteristics can be figured out.

The above descriptions are only a preferred embodiment of the present invention. It should be noted that those of ordinary skill in the art can also make several improvements and modifications without departing from the principles of the present invention, and these improvements and modifications should also be regarded as the scope of protection of the present invention.

Embodiment 3

A method for evaluating an anchoring and grouting reinforcement effect based on drilling parameters includes the following specific steps:

Step 1: taking onsite fractured rocks in an underground engineering, manufacturing indoor drilling test pieces, dividing the indoor drilling test pieces into several groups and each of which includes 15 test pieces;

step 2: taking any group as an example, randomly taking three test pieces, implementing an indoor drilling test, recording the drilling parameters of the three test pieces, substituting the drilling parameters of each test piece into the optimal regression relational expression of the uniaxial compressive strength and the drilling parameters in the step 5) in the second solution to obtain the equivalent uniaxial compressive strength of each test piece, and then obtaining a representative value of the equivalent uniaxial compressive strength of the group of the fractured rock masses;

step 3: comparing the representative value of the equivalent uniaxial compressive strength obtained in the step 2 with an expected strength value, designing an anchoring and grouting solution, implementing the same anchoring and grouting reinforcement solution on the rest test pieces in the group, including the slurry-water-cement ratio, the grouting pressure, the anchor rod length and the anchor rod diameter and curing the test pieces under the same conditions;

step 4: performing the indoor drilling test on the cured reinforced test piece, and substituting the drilling parameters into the optimal regression relational expression of the uniaxial compressive strength and the drilling parameters in the step 5 of solution 2 to obtain the equivalent uniaxial compressive strength of each test piece;

step 5: calculating a guarantee rate of the equivalent uniaxial compressive strength after the reinforcement of the group of test pieces, if the guarantee rate is greater than 95%, judging that the grouting reinforcement solution is reasonable, or otherwise, judging that the grouting reinforcement solution is unreasonable. The calculation formula of the guarantee rate of the equivalent uniaxial compressive strength of the reinforced test piece is:

$$\lambda = \frac{num}{N} \times 100\%$$

In which num represents the number of reinforced test pieces with equivalent uniaxial compressive strength greater than the expected strength value in the group, and N represents the total number of the reinforced test pieces in the group.

The above descriptions are only preferred embodiments of the present invention. It should be noted that those of ordinary skill in the art can also make several improvements and modifications without departing from the principles of the present invention, and these improvements and modifications should also be regarded as the scope of protection of the present invention.

The invention claimed is:

1. A test method for characterizing rock mass characteristics by using drilling parameters in underground engineering, wherein rock cores are respectively taken from a plurality of drilling holes on the same test piece, a uniaxial test and a triaxial test being respectively performed on the rock cores to obtain multiple groups of mechanical property parameters, multiple groups of drilling parameters being obtained by a multifunctional true triaxial rock drilling test system, a relational expression between mechanical property parameters of rock mass and the drilling parameters being established, and the mechanical property parameters of rock mass is obtained by detecting the drilling parameters of the rock mass through the relational expression, the multifunctional true triaxial rock drilling test including a pressure loading device that applies a confining pressure to the rock test piece placed therein, a drilling rig unit that is arranged at an upper end of the pressure loading device for drilling the rock test piece under pressure, a monitoring control unit that controls the pressure loading device to apply the pressure and controls either of two groups of values of the drilling rig unit, which include a torque and a rotating speed, and a drilling pressure and a displacement, and a hydraulic station that provides power for the pressure loading device, the test method comprising steps as follows:

step 1) according to a test purpose, determining rock mass basic factors affecting three-way confining pressure loading drilling, and designing a reasonable test solution;

step 2) preparing the corresponding test piece according to the test solution;

step 3) performing a three-way confining pressure drilling test on the prepared test piece, collecting the drilling parameters in a drilling process of the test piece in the test, and collecting the rock core of the test piece;

step 4a) performing statistics on a core collection rate of the rock core of the test piece, and measuring a integrity parameter RQD value of the test piece;

step 4b) cutting and grinding the rock core obtained from the test piece, manufacturing a plurality of standard test pieces, and performing the triaxial test and a uniaxial test to measure the mechanical property parameters of the test piece material; and step 5) preprocessing the collected data, and then establishing the relationship between the processed data and the same-depth rock mechanical properties and rock mass integrity parameters, including an optimal regression relational expression of the uniaxial compressive strength and the drilling parameters, the optimal regression relational expression of a cohesive force and the drilling parameters, the optimal regression relational expression of an inner friction angle and the drilling parameters, the optimal regression relational expression of modulus of elasticity and the drilling parameters, a rock mass integrity parameter RQD value, a torque fracture index $QD_m$ and a rotating speed fracture index $QD_r$.

2. The test method according to claim 1, wherein the pressure loading device includes a pressure chamber, and a confining pressure loading device is arranged on an outer side of the pressure chamber to apply the confining pressure to the rock test piece, and a test piece platform for carrying the pressure chamber and the rock test piece is arranged at the lower end of the pressure chamber.

3. The test method according to claim 2, wherein the confining pressure loading device includes two groups of vertically arranged lateral loading plates, each group of lateral loading plates includes two opposite lateral loading plates arranged in parallel, and the two groups of lateral loading plates form a rectangular loading structure to surround the test piece in the pressure chamber, the confining pressure loading device further includes a lateral hydraulic oil cylinder, the hydraulic oil cylinder drives a piston rod to push the lateral loading plate to apply a horizontal pressure to the test piece, and a lateral reaction force plate is arranged on the outer side of the lateral hydraulic oil cylinder.

4. The test method according to claim 1, wherein the drilling rig unit includes a drilling rig embedded in a drilling rig slide rail, the drilling rig axially moves up and down along the drilling rig slide rail, and the drilling rig slide rail is fixed on a reaction force frame at a top of the test piece through a drilling rig slide rail fixing plate.

5. The test method according to claim 4, wherein the drilling rig unit further includes a servo motor, a speed reduction mechanism, and a belt transmission device, the belt transmission device and the speed reduction mechanism constitute a two-stage speed reduction mechanism, the speed reduction multiples are changed with a diameter ratio of gears at both ends of a belt in the belt transmission device, a upper part of the drilling rig is fixedly connected to a drilling rig top hydraulic oil cylinder, the drilling rig top hydraulic oil cylinder provides an axial force for the drilling rig, and the drilling rig servo motor provides a rotating force for the drilling rig.

6. The test method according to claim 1, wherein:
the monitoring control unit includes a monitoring unit, and lateral confining pressure sensors for detecting lateral confining pressure of four directions, a lateral displacement sensor for detecting a moving distance of the lateral loading plate, and a drilling rig torque sensor for detecting the torque of the drilling rig, a drilling rig rotating speed sensor for detecting the rotating speed of the drilling rig, a drilling rig pressure sensor for detecting pressure applied by the drilling rig downward, and a drilling rig displacement sensor for detecting the vertical moving distance of the drilling rig; and
the servo motor has a rotating speed sensor.

7. The test method according to claim 6, further comprising an axial pressure loading device for applying an axial pressure to the rock test piece, wherein the axial pressure loading device includes an axial hydraulic oil cylinder, an axial loading plate is arranged at the lower part of the test piece, and the axial hydraulic oil cylinder pushes the axial loading plate to drive the rock test piece to perform axial movement and contacts the reaction force frame to apply an axial force to the rock test piece.

8. The test method according to claim 7, further comprising an axial pressure sensor arranged at the axial hydraulic oil cylinder, wherein the lateral confining pressure sensor is arranged on an oil supply pipeline, and the lateral displacement sensor is arranged on the side of the lateral hydraulic oil cylinder.

9. The test method according to claim 8, wherein the monitoring control unit includes a control unit including a logic controller, a power amplifier and a servo motor, the logic controller receives signals of the sensors, compares the signals with a set value, sends a voltage instruction to control the drilling rig servo motor and the hydraulic station servo motor to work, and achieves closed-loop control, and the hydraulic station servo motor is connected with the axial hydraulic oil cylinder and the lateral hydraulic oil cylinder respectively.

10. The test method according to claim 9, wherein:
the control unit controls the drilling rig in four modes:
A. controlling a torque and a drilling rate, and collecting a drilling pressure and a rotating speed;
B. controlling the torque and the drilling pressure, and collecting a rotating speed and a drilling rate;
C. controlling the rotating speed and the drilling rate, and collecting the torque and the drilling pressure; and
D. controlling the rotating speed and the drilling pressure, and collecting the torque and the drilling rate; and
the control unit controls the hydraulic station servo motor to control the axial pressure and the confining pressure of the test piece in three control modes:
A. a constant strain loading mode, in which small strains occurring in the test piece within a unit time are the same;
B. a constant pressure incremental loading mode, in which the pressure increase of the hydraulic oil cylinder within the unit time is the same; and
C. a constant force maintenance mode, in which the test piece is kept at a set confining pressure value.

11. The test method according to claim 10, wherein the control of constant strain loading of the test piece is as follows:
the axial loading device pushes the pressure chamber to ascend, so that the top of a uniaxial test piece contacts a platform plate below the reaction force frame, the uniaxial test piece is in a uniaxial compression state,
the axial loading device is controlled to be in a constant strain loading mode, and
the axial pressure is applied to the test piece at a loading speed suggested by the International Society for Rock Mechanics until the test piece is broken.

12. The test method according to claim 10, wherein the control of constant pressure incremental loading of the test piece is as follows: three main stresses are independently applied to the rock mass test piece, the constant pressure incremental loading is that the same pressure is applied to a certain side face of the test piece within the unit time; and the working method is that the logic controller records the current pressure read by the lateral pressure sensor or the axial pressure sensor, and controls the servo motor to drive the oil cylinder to pressurize the test piece, the logic controller records the pressure change of the pressure sensor, and when the pressure reaches a preset increment within a unit time, the logic controller controls the servo motor to stop and repeats the above work within the next unit time.

13. The test method according to claim 1, wherein the integrity parameter RQD value of rock mass is obtained by detecting the drilling parameters of the rock mass through the relational expression.

14. The test method according to claim 1, wherein the rock core is divided into multiple segments from top to bottom, and the mechanical property parameters of the segments are obtained respectively.

15. The test method according to claim 1, wherein the relationship between the rock mass integrity parameter RQD value and the drilling parameters is established; on the basis of a large number of test data, formula fitting is performed on the RQD value of the test piece, the torque fracture index $QD_m$ and the rotating speed fracture index $QD_r$ by using a multiple linear regression method; and the final form of the fitting formula is:

$$RQD=\beta_0+\beta_1 QD_m+\beta_2 QD_r.$$

wherein $\beta_0$, $\beta_1$ and $\beta_2$ all represent regression coefficients.

16. The test method according to claim 15, wherein the torque fracture index $QD_m$ and a rotating speed fracture index $QD_r$ are calculated by using the following formulas:

$$QD_m = \frac{\Sigma h_i^1 + \Sigma l_j^1}{H}$$

$$QD_r = \frac{\Sigma h_i^2 + \Sigma l_j^2}{H}$$

in which $h_i^1$ represents the length of the ith segment of which the torque significant rate $\overline{m}$ is less than the critical value in a certain drilling hole, $l_i^1$ represents the length of the jth segment of which the torque significant rate index is greater than the critical value and the length is less than 100 mm, $h_i^2$ represents the length of the ith segment of which the rotating speed significant rate $\overline{m}$ is greater than the critical value in a certain drilling hole, $l_i^2$ represents the length of the jth segment of which the rotating speed significant rate index is greater than the critical value and the length is less than 100 mm, and H represents the total length of a certain drilling hole.

17. A method for evaluating an anchoring and grouting reinforcement effect based on drilling parameters, the evaluating method being based on based on a multifunctional true triaxial rock drilling test system, the multifunctional true triaxial rock drilling test including a pressure loading device that applies a confining pressure to a rock test piece placed therein, a drilling rig unit that is arranged at an upper end of the pressure loading device for drilling the rock test piece under pressure, a monitoring control unit that controls the pressure loading device to apply the pressure and controls either of two groups of values of the drilling rig unit, which include a torque and a rotating speed, and a drilling pressure and a displacement, and a hydraulic station that provides power for the pressure loading device, the method performing an indoor drilling test on the rock test piece obtained onsite before and after anchoring and grouting reinforcement, designing an anchoring and grouting reinforcement solution according to a representative value of the equivalent uniaxial compressive strength of the test piece before the anchoring and grouting reinforcement, and determining the reasonableness of the anchoring and grouting reinforcement solution via a guarantee rate $\lambda$ of the equivalent uniaxial compressive strength after the test piece is reinforced, the method comprising the following specific steps:

Step A): taking onsite fractured rocks in an underground engineering, manufacturing indoor drilling test pieces, and dividing the indoor drilling test pieces into several groups;

step B): taking any group as an example, randomly taking a part of test pieces, implementing an indoor drilling test, recording the drilling parameters of three test pieces, substituting the drilling parameters of each test piece into the optimal regression relational expression of the uniaxial compressive strength and the drilling parameters of preprocessing the collected data, and then establishing the relationship between the processed data and the same-depth rock mechanical properties and rock mass integrity parameters, including an optimal regression relational expression of the uniaxial compressive strength and the drilling parameters, the optimal regression relational expression of a cohesive force and the drilling parameters, the optimal regression relational expression of an inner friction angle and the drilling parameters, the optimal regression relational expression of modulus of elasticity and the drilling parameters, a rock mass integrity parameter RQD value, a torque fracture index $QD_m$ and a rotating speed fracture index $QD_r$ to obtain the equivalent uniaxial compressive strength of each test piece, and then obtaining a representative value of the equivalent uniaxial compressive strength of the group of fractured rock masses;

step C): comparing the representative value of the equivalent uniaxial compressive strength obtained in the step B) with an expected strength value, designing an anchoring and grouting solution, implementing the same anchoring and grouting reinforcement solution on the rest test pieces in the group, and curing the test pieces under the same conditions;

step D): performing the indoor drilling test on the cured reinforced test piece, and substituting the drilling parameters into the optimal regression relational expression of the uniaxial compressive strength and the drilling parameters of preprocessing the collected data, and then establishing the relationship between the processed data and the same-depth rock mechanical properties and rock mass integrity parameters, including an optimal regression relational expression of the uniaxial compressive strength and the drilling parameters, the optimal regression relational expression of a cohesive force and the drilling parameters, the optimal regression relational expression of an inner friction angle and the drilling parameters, the optimal regression relational expression of modulus of elasticity and the drilling parameters, a rock mass integrity parameter RQD value, a torque fracture index $QD_m$ and a rotating speed fracture index $QD_r$ to obtain the equivalent uniaxial compressive strength of each test piece; and step E): calculating a guarantee rate of the equivalent uniaxial compressive strength after the reinforcement of the group of test pieces, if the guarantee rate is greater than 95%, judging that the anchoring and grouting reinforcement solution is reasonable, or otherwise, judging that the anchoring and grouting reinforcement solution is unreasonable.

18. The method for evaluating the anchoring and grouting reinforcement effect based on drilling parameters according to claim 17, wherein the calculation method of the equivalent compressive strength of the test piece in the step C) comprises: substituting the drilling parameters, including the torque m, the rotating speed r, the drilling pressure n, drilling speed v and the drilling specific work w of the drilling rig into the optimal regression relational expression of the uniaxial compressive strength and the drilling parameters preprocessing the collected data, and then establishing the relationship between the processed data and the same-depth rock mechanical properties and rock mass integrity parameters, including an optimal regression relational expression of the uniaxial compressive strength and the drilling parameters, the optimal regression relational expression of a cohesive force and the drilling parameters, the optimal regression relational expression of an inner friction angle and the drilling parameters, the optimal regression relational expression of modulus of elasticity and the drilling parameters, a rock mass integrity parameter RQD value, a torque fracture index $QD_m$ and a rotating speed fracture index $QD_r$ to obtain the equivalent uniaxial compressive strength of each test piece.

19. The method for evaluating the anchoring and grouting reinforcement effect based on drilling parameters according to claim 17, wherein the representative value of the equivalent uniaxial compressive strength of the fractured rock mass is represented by the average value of the equivalent compressive strength of part of test pieces; if the deviation between the maximum value and the average value or between the minimum value and the average value is greater than 15%, an intermediate value is used as the representative value, and if the deviations between the maximum value and the average value and between the minimum value and the average value are both greater than 15%, the group of data is invalid.

20. The method for evaluating the anchoring and grouting reinforcement effect based on drilling parameters according to claim 17, wherein the anchoring and grouting reinforcement solution is to determine a slurry-water-cement ratio, a grouting pressure, an anchor rod length and an anchor rod diameter.

21. The method for evaluating the anchoring and grouting reinforcement effect based on drilling parameters according to claim 17, wherein the calculation method of the guarantee rate of the equivalent uniaxial compressive strength is:

$$\lambda = \frac{num}{N} \times 100\%$$

in which num represents the number of reinforced test pieces with equivalent uniaxial compressive strength greater than the expected strength value in the group, and N represents the total number of the reinforced test pieces in the group.

* * * * *